United States Patent
Jonson et al.

(10) Patent No.: US 9,861,335 B2
(45) Date of Patent: Jan. 9, 2018

(54) MAMMOGRAPHIC TOMOGRAPHY TEST PHANTOM

(71) Applicant: University of the Free State, Bloemfontein (ZA)

(72) Inventors: Bernine Jonson, Durban (ZA); William Ian Duncombe Rae, Bloemfontein (ZA)

(73) Assignee: UNIVERSITY OF THE FREE STATE, Bloemfontein (ZA)

( * ) Notice: Subject to any disclaimer, the term of this patent is extended or adjusted under 35 U.S.C. 154(b) by 272 days.

(21) Appl. No.: 14/436,050

(22) PCT Filed: Sep. 6, 2013

(86) PCT No.: PCT/IB2013/058344
§ 371 (c)(1),
(2) Date: Apr. 15, 2015

(87) PCT Pub. No.: WO2014/041469
PCT Pub. Date: Mar. 20, 2014

(65) Prior Publication Data
US 2015/0272535 A1 Oct. 1, 2015

(30) Foreign Application Priority Data
Sep. 13, 2012 (ZA) .................. 2012/06864

(51) Int. Cl.
*G06K 9/00* (2006.01)
*A61B 6/00* (2006.01)
(Continued)

(52) U.S. Cl.
CPC .............. *A61B 6/583* (2013.01); *A61B 6/025* (2013.01); *A61B 6/502* (2013.01); *A61B 6/5205* (2013.01);
(Continued)

(58) Field of Classification Search
CPC ......... A61B 6/583; A61B 6/025; A61B 6/502; A61B 6/5205; G06T 7/0014;
(Continued)

(56) References Cited

U.S. PATENT DOCUMENTS 5,095,499 A 3/1992 Wentz
5,165,050 A * 11/1992 Goodenough ......... G01R 33/58
324/318

(Continued)

OTHER PUBLICATIONS

Mammographic Accreditation Phantom, 2003, Elimpex, pp. 1-18.*
(Continued)

*Primary Examiner* — Jonathan S Lee
(74) *Attorney, Agent, or Firm* — John P. White; Cooper & Dunham LLP

(57) ABSTRACT

This invention relates to a mammographic tomography test object (hereinafter referred to as a phantom) and more particularly, but not exclusively, to a mammographic tomography test phantom for use in the verification of image reconstruction positions in digital breast tomosynthesis. The phantom includes a body made from an approximately tissue equivalent x-ray attenuating material; an upper spacer located on top of the body, and a lower spacer located below the body, the spacers being made from a substantially non-compressible material; and a plurality of x-ray opaque granules located at predetermined positions within the body.

13 Claims, 3 Drawing Sheets

(51) Int. Cl.
*A61B 6/02* (2006.01)
*G06T 7/00* (2017.01)
*G06T 11/00* (2006.01)

(52) U.S. Cl.
CPC .......... *G06T 7/0014* (2013.01); *G06T 11/008* (2013.01); *G06T 2207/10081* (2013.01); *G06T 2207/10112* (2013.01); *G06T 2207/30068* (2013.01)

(58) Field of Classification Search
CPC ......... G06T 11/008; G06T 2207/10081; G06T 2207/10112; G06T 2207/30068
See application file for complete search history.

(56) References Cited

U.S. PATENT DOCUMENTS

| | | | | |
|---|---|---|---|---|
| 6,885,724 | B2* | 4/2005 | Li | A61B 6/025 378/2 |
| 8,517,608 | B1* | 8/2013 | Arnold | A61B 6/032 378/207 |
| 2003/0058999 | A1* | 3/2003 | Mitschke | A61B 6/583 378/207 |
| 2005/0207630 | A1* | 9/2005 | Chan | A61B 6/466 382/131 |
| 2009/0171244 | A1 | 7/2009 | Ning et al. | |
| 2011/0142316 | A1* | 6/2011 | Wang | G06T 11/006 382/131 |
| 2011/0305313 | A1* | 12/2011 | Sklansky | A61B 6/0414 378/37 |
| 2012/0207283 | A1 | 8/2012 | Muller et al. | |
| 2015/0305705 | A1* | 10/2015 | Goodenough | A61B 6/025 378/207 |

OTHER PUBLICATIONS

Hamza, Alnazier OM. "The design and fabrication of a full field quantitative mammographic phantom." Biomedical Engineering Conference, 2008. CIBEC 2008. Cairo International. IEEE, 2008.*
Vieira, Silvio L., et al. "Paraffin-gel tissue-mimicking material for ultrasound-guided needle biopsy phantom." Ultrasound in medicine & biology 39.12 (2013): 2477-2484.*
Srinivasan, R., and Megha Singh. "Laser backscattering and transillumination imaging of human tissues and their equivalent phantoms." IEEE transactions on biomedical engineering 50.6 (2003): 724-730.*
Sobotka, Piotr Kamil, et al. "Breast phantom for comparison X-ray and polarimetric optical tomography imaging." Photonics Letters of Poland 4.1 (2012): 38-40.*
Cubukcu, Solen, and H. Yücel. "Development of breast tissue equivalent phantom made from paraffin with some additives and its characterization by using X-ray spectroscopy." ECR, 2015.*
Bertolini, Marco, et al. "Contrast detail phantom comparison on a commercially available unit. Digital breast tomosynthesis (DBT) versus full-field digital mammography (FFDM)." Journal of digital imaging 24.1 (2011): 58-65.*
Computerized Imaging Reference Systems, Tissue Equivalent Mammography QA Phantom, 2008, pp. 1-16.*
Gammex, Mammography QA Solutions, 2015, pp. 1-8.*
International Search Report, dated Dec. 20, 2013 in connection with PCT International Application No. PCT/IB2013/058344, filed Sep. 6, 2013.
Written Opinion of the International Searching Authority, dated Dec. 20, 2013 in connection with PCT International Application No. PCT/IB2013/058344, filed Sep. 6, 2013.
Notification Concerning Transmittal of International Preliminary Report on Patentability (Chapter I of the Patent Cooperation Treaty), including an International Preliminary Report on Patentability and Written Opinion of the International Searching Authority, dated Mar. 17, 2015 by The International Bureau of WIPO in connection with PCT International Application No. PCT/IB2013/058344, filed Sep. 6, 2013.

* cited by examiner

MAMMOGRAPHIC TOMOGRAPHY TEST PHANTOM

CROSS-REFERENCE TO RELATED APPLICATIONS

This application is a §371 national stage of PCT International Application No. PCT/IB2013/058344, filed Sep. 6, 2013, claiming priority of South African Patent Application No. 2012/06864, filed Sep. 13, 2012, the contents of each of which are hereby incorporated by reference in their entirety.

BACKGROUND TO THE INVENTION

THIS invention relates to a mammographic tomography test object (hereinafter referred to as a phantom) and more particularly, but not exclusively, to a mammographic tomography test phantom for use in the verification of image reconstruction positions in digital breast tomosynthesis. The invention also relates to a method of verifying image reconstruction positions in digital breast tomosynthesis using a customized mammographic tomography test phantom.

Breast cancer is one of the most common cancers affecting women all over the world. Early detection is vital so that the patient can be diagnosed and treated, as the chance of survival is much better when breast cancer is detected at an early stage. Over the past few years advances in technology have ensured an increase in the development and uptake of mammography systems.

In standard two dimensional (2D) projection film screen mammography (FSM) or full field digital mammography (FFDM), overlapping dense fibroglandular tissue within the breast can reduce the visibility of malignant abnormalities or can simulate the appearance of an abnormality. This can lead to unnecessary recalls, biopsies and psychological stress for the women concerned. In this conventional mammography, overlapping or superimposed tissue creates a clutter of signals above and below objects of interest, which can for example result in lesions being hidden by other objects.

Digital breast tomosynthesis (DBT) is a relatively newly developed form of three dimensional (3D) image reconstruction which has the potential of improving the accuracy of mammography by blurring out overlying tissues. It is based on the outdated linear tomographic technique (superseded by Computed Tomography (CT) scanning) that was used in the 1970s to achieve an equivalent goal in general x-ray imaging. The overlying tissue in the image, sometimes referred to as anatomical noise, degrades image quality in standard 2D projection imaging. The definition of tomosynthesis, as stated in the LORAD Hologic Selenia Dimensions Quality Control manual is "an imaging technique that recombines a number of breast images taken at different angles through the breast to achieve various effects". In DBT, multiple projection images of the breast (approximately 15) are acquired from different angulations of the x-ray tube within a single plane of motion perpendicular to the detector and in line with the front edge of the detector. The images are then processed using reconstruction algorithms to produce tomographic sections through the breast. These sections can be viewed on a computer as planes or slices. By reducing the superimposition of overlying breast tissue, DBT has the potential to differentiate malignant features more definitively from non-malignant ones. It should be noted that the improvements to linear tomography (originally developed in the 70's) included non-linear translations which increased out of reconstruction plane image blur thus improving in reconstruction plane resolution. These non-linear translations included circular and hyper-cycloidal movements.

It is obvious that, as with any other form of radiology, in DBT image quality is very important and should be optimized. Various parameters influence the image quality, two of which are the angular range of the x-ray tube, and the number of exposures. These parameters are usually fixed on any particular DBT system, but have a huge impact on image quality The larger the angular range, the wider the separation of the slices and increase in the out of plane resolution. However, with smaller angles more structures will be in focus in a specific plane. More angles at which images are acquired will result in more exposures which would reduce the visibility of artefacts, but more ionising radiation dose will be delivered to the patients. Compensation by reducing the dose per view is limited as this will introduce more statistical noise in the image and may at some point start to deteriorate image quality.

An artefact, in the radiological sense, refers to any perceived structure that is not actually present, but is produced by the imaging process, i.e. something not anatomically real such as the distortion of a structure or signal, which interferes with or obscures the interpretation of a study, or a structure that is not representative of a specimen's in vivo state and which does not reflect the original sample, but rather is the result of an imaging procedure, its analysis or other factors. The smearing/out of plane artefact is one of the most prominent artefacts found in DBT. These artefacts may thus lead to uncertainties in where the planes are in DBT, as well as how accurately the reconstruction plane can be said to be a fixed thickness, such as 1 mm slice thickness. Therefore, for the image quality to be optimized the image reconstruction plane position and characteristics need to be defined. This uncertainty should be quantified as part of the quality program for DBT systems, to determine accurately the actual image reconstruction planes (IRP) obtained during tomographic reconstruction.

It is accordingly an object of the invention to provide a mammographic tomography test phantom for use in the verification of image reconstruction depths in digital breast tomosynthesis, which will enable the accurate determination of image reconstruction planes.

It is also an object of the invention to provide a method of verifying image resolution at various positions in digital breast tomosynthesis images by customizing the mammographic tomosynthesis test phantom, and developing an appropriate analysis algorithm, which method will enable the quantification of image resolution degradation at various points and in two planes in the image (in the plane of motion and perpendicular to the plane of motion of the DBT x-ray source).

SUMMARY OF THE INVENTION

According to the invention there is provided a mammographic tomography test phantom for use in the verification of image reconstruction positions in digital breast tomosynthesis, the phantom including:
 a body made from an approximately tissue equivalent x-ray attenuating material;
 an upper spacer located on top of the body, and a lower spacer located below the body, the spacers being made from a substantially non-compressible material;
 and a plurality of x-ray opaque granules located at predetermined positions within the body.

There is provided for the positions of the granules to be dependent on their depth within the body.

There is provided for the body to be made from wax, and more particularly for the body to comprise a plurality of wax layers located on top of one another.

The x-ray opaque nodules may be impregnated into the wax sheets at predetermined intervals and locations.

Each wax layer may be in the form of a singular sheet of wax, or may be made up of a set of thinner wax sheets.

Each wax layer may a unique identifier. The identifier may be in the form of a particular number and/or configuration of x-ray opaque nodules provided in an end zone of the wax layer.

Where the wax layer comprises a set of wax sheets, each wax sheet of the set may further include a particular number and/or configuration of x-ray opaque nodules that identifies the individual sheets within a set.

There is provided for the x-ray opaque nodules to be diagonally offset in order to reduce superposition of projection artefacts.

The x-ray opaque nodules may be in the form of marble granules, and may be between 100 and 300 μm, and more preferably between 200 and 250 μm so as to test the range of resolutions expected from mammographic tomography units.

The spacers, which allow for accurate offset correction, are made from planar, substantially non-compressible material, for example paper, card, Perspex® or another suitable plastic.

BRIEF DESCRIPTION OF THE DRAWINGS

Embodiments of the invention are described by way of example only, and with reference to the accompanying figures, in which.

DESCRIPTION OF THE INVENTION

As has been stated above, image quality is of utmost importance when assessing the results of DBT. Therefore, in order for the image quality to be optimized, the image reconstruction plane needs to be known. This uncertainty should be quantified as part of the quality program for DBT systems, to determine accurately the actual positions of image reconstruction planes (IRP) obtained during tomographic reconstruction. The object of this invention is therefore to determine the vertical positioning of reconstruction planes in DBT using a purpose built phantom.

The LORAD Hologic Selenia Dimensions mammography unit at Universitas Hospital in Bloemfontein, South Africa was used for the purposes of testing and validating the proposed technology, and in particular the new purpose built phantom unit. Images were obtained using the tomosynthesis function with exposures determined using automatic exposure control. The images were displayed and analysed on Mammographic reporting screens.

The composition of a first embodiment of a phantom is now discussed with reference to FIG. 1. In order to assess the image quality the test object had to be positioned accurately within the image reconstruction plane (IRP). Therefore the IRP had to be accurately known and used during imaging. A phantom 10 was built using cards 21, wax sheets 31 and 200-250 μm calcifications 40 (ground marble sieved to form marble specs which are composed of $CaCO_3$). This size of calcifications was selected because in the selected range the calcifications were big enough to handle but small enough not to cause a partial volume effect (smallest amount of artefacts). The calcifications were also larger than a pixel. In one embodiment of the invention the opaque nodules were composed of crushed and sifted marble granules (micro-calcification analogues) of diameter 125-150 μm and 200-250 μm respectively. The atomic components within the marble used were almost 98% calcium carbonate, with magnesium comprising <2% as the second major component of the dried crushed sample analysed.

Figure 1:
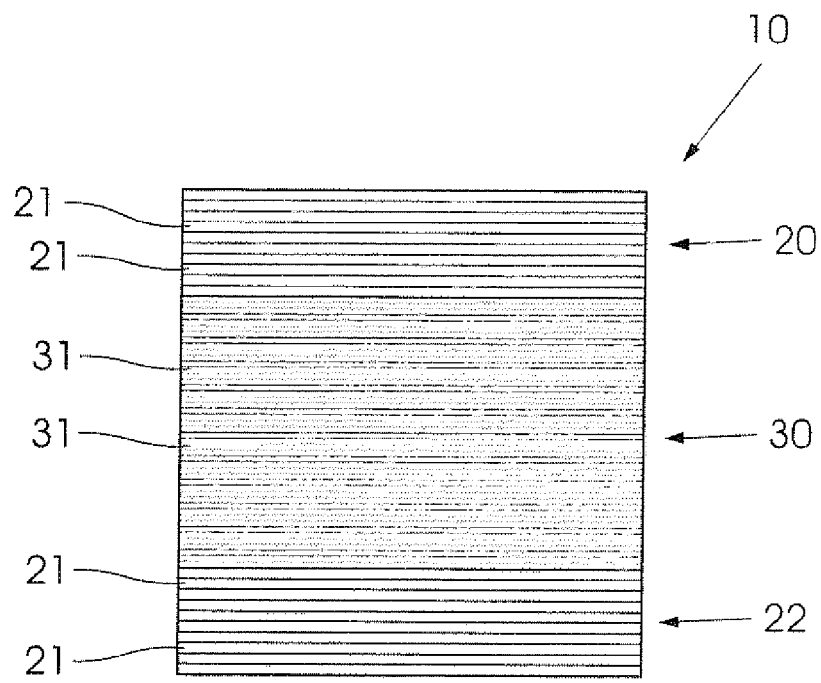
FIG. 1 is a schematic cross-sectional side view of one embodiment of the phantom in accordance with one embodiment of the invention.

In the embodiment of FIG. 1 forty paper cards 21 were used at the lower end of the phantom 10 in order to form a bottom layer 22, and forty paper cards 21 were used at the upper end of the phantom 10 in order to form a top layer 20. Each set of cards were 9.60 mm±0.05 mm thick. Twenty wax sheets 31 were sandwiched between the top layer 20 and the bottom layer 22 so as to form a layered body 30 having a combined thickness of about 30.4 mm±0.05 mm. This means that each wax sheet has a thickness of about 1.50 mm±0.05 mm. The error in the thickness measurement of the phantom was in the order of 0.05 mm. One embodiment of the phantom used dental modelling wax sheets, "Cavex Set Up Hard" Cavex Holland BV, of dimension 190×90×1 mm.

Figure 2:
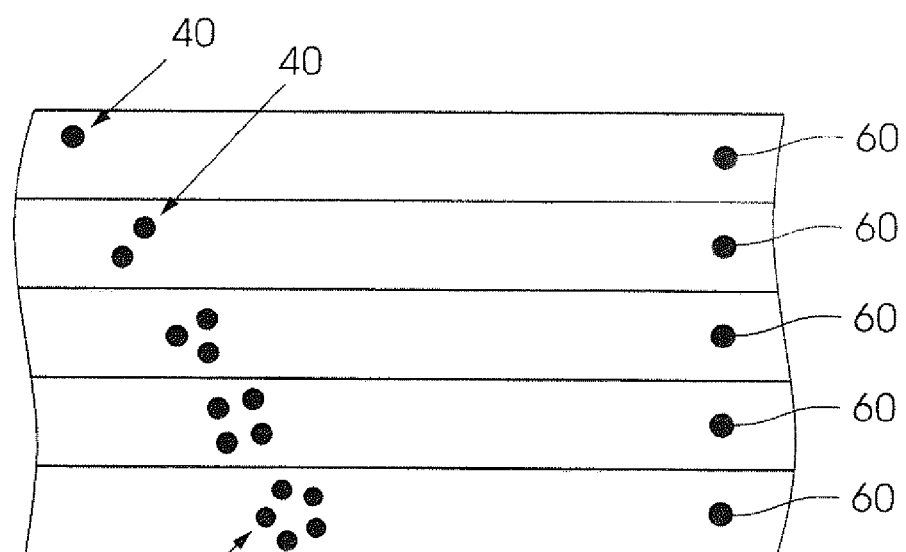
FIG. 2 is a schematic representation showing the patterns of the calcifications positioned in the wax body of FIG. 1.

The calcifications 40 were arranged in different patterns and at different depths in the layered body 30, which allowed the accurate identification of specific slices according to the predetermined and configured pattern present at the different layers. The calcifications 40 were placed in patterns as shown in FIG. 2. The first wax sheet had one calcification and in the opposite end had another one to represent the first set of wax sheets. Each set comprised five wax sheets and each set was distinguished according to the number of calcifications on the opposite end. The calcifications were placed so as to ensure that the smear artefact did not interfere with adequate interpretation of the images.

Figure 4:
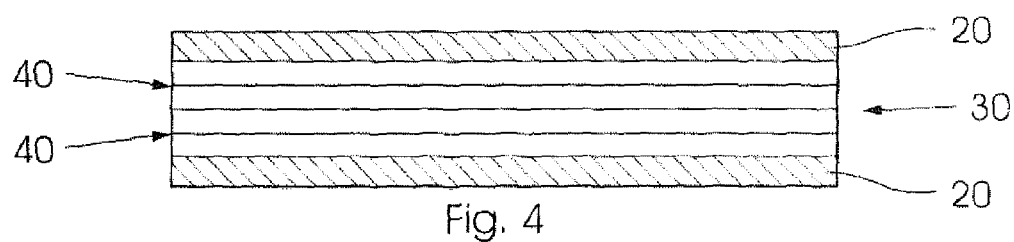
FIG. 4 is a schematic cross-sectional side view of another embodiment of the phantom in accordance the invention.
Figure 6:
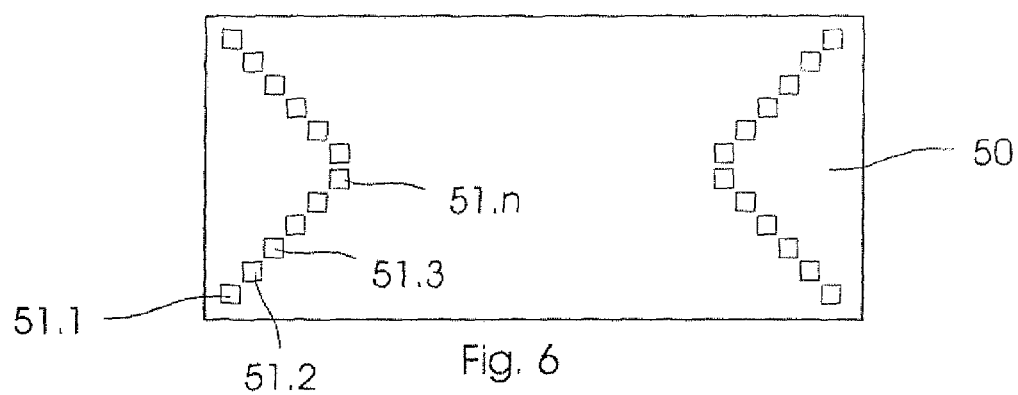
FIG. 6 is a plan view of a template used to position the calcifications in the wax body.

In the embodiment of FIG. 4, a Perspex® container with 1.5 mm and 2 mm thick front and back plates was constructed to protect the wax block and to adjust the position of the lowest layer of granules to be in a reconstruction plane. Four thick wax layers were used to make up the wax body 30, instead of the plurality of wax sheets described above. The calcifications were positioned between the four wax layers using the template shown in FIG. 6, and which shows the diagonally offset between calcifications position on different levels. The first identifier (which will constitute a single calcification) will be located inside the cut-out 51.1. The second identifier (which will constitute two calcifications arranged in a configuration where the two calcifications are not in the same horizontal plane) will be located in cut-out 51.2. This is repeated until the $n^{th}$ layer is reached, and the $n^{th}$ identifier is located in cut-out 51.n.

Figure 5:
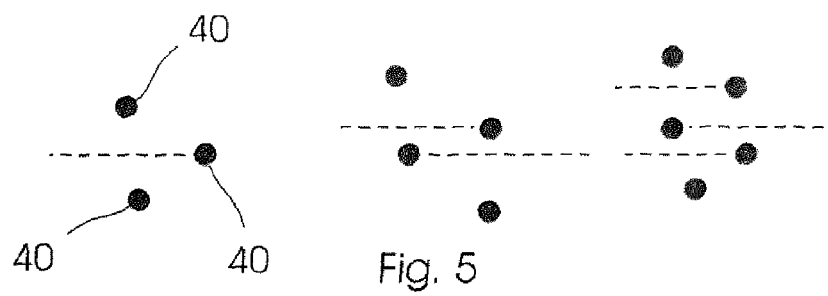
FIG. 5 illustrates the configuration of the calcifications used to denote different levels.

In both the embodiments (i.e. FIG. 1 or FIG. 4) the correct configuration of the calcifications is important, and more particularly, care should be taken not to position calcifications of a particular set (or number) in such a way where some of the calcifications in the set horizontally overlaps, because this will result in smearing. As shown in the three examples if FIG. 5, none of the calcifications making up each one of the three identifiers are in the same horizontal plane.

The phantom of the first embodiment was placed on the breast support of the mammography unit, and compressed. The automatic exposure control mode was used, and the images were then sent to the picture archiving and communication system and analysed. There were 52 slices and the real positions of the calcifications were determined by getting all the groups of calcifications in the right focal plane.

The algorithm used to analyse the resolution in two planes for each plane is summarised below:
1. Within the image set file, identify the basal plane of the object.
2. Using edge detection find the left and right edges and the front and back edges of the object.
3. From the known size of the phantom calculate the magnification of the object in the in-plane and front-back (Anterior-posterior) axes of the image set and determine the apparent pixel size.
4. For each nominal slice of interest (where the granules have been placed), and the slice above and below each of these slices: Step to the corner of the appropriate block where the small opaque grains are positioned (See FIG. 3), using the scale factors determined above.
5. Step through a 6×6 mm sub-image using a single pixel step size in both directions sequentially and perform template matching using a symmetric, two dimensional, pixelated, Gaussian template of size 400×400 mm.
6. Determine the maxima and full width half maxima of the identified granules in the in-plane and front-back axes for all slices.
7. Confirm identity of the slice position from the number and position of the maxima within the sub-images.
8. Subtract the mean background signal.
9. Ratios can be used to determine contrast, relative resolution, and artefact distortion of the image due to the in-plane blurring.
10. Identify from the ratios if the resolution is best within the appropriate slice.

The result obtained using the phantom is shown in table 1, which includes the slice numbers, the best seen image position of the calcification as well as the standard deviation obtained from the slice number and position in the slice.

TABLE 1

The obtained slice number and the best seen images of the calcifications in the slice

| Slice number | Position 1.50 (mm) | STD % |
|---|---|---|
| 11 | 11.1 | 0.07 |
| 12 | 12.6 | 0.42 |
| 13 | | |
| 14 | 14.1 | 0.07 |
| 15 | 15.6 | 0.42 |
| 16 | | |
| 17 | 17.1 | 0.07 |
| 18 | | |
| 19 | 18.6 | 0.28 |
| 20 | 20.1 | 0.07 |
| 21 | 21.6 | 0.42 |
| 22 | | |
| 23 | | |
| 24 | 23.1 | 0.64 |

TABLE 1-continued

The obtained slice number and the best seen images of the calcifications in the slice

| Slice number | Position 1.50 (mm) | STD % |
|---|---|---|
| 25 | 24.6 | 0.28 |
| 26 | 26.1 | 0.07 |
| 27 | 27.6 | 0.42 |
| 28 | | |
| 29 | 29.1 | 0.07 |
| 30 | 30.6 | 0.42 |
| 31 | 32.1 | 0.78 |
| 32 | | |
| 33 | 33.6 | 0.42 |
| 34 | | |
| 35 | 35.1 | 0.07 |
| 36 | 36.6 | 0.42 |
| 37 | | |
| 38 | 38.1 | 0.07 |
| 39 | 39.6 | 0.42 |

Figure 3:
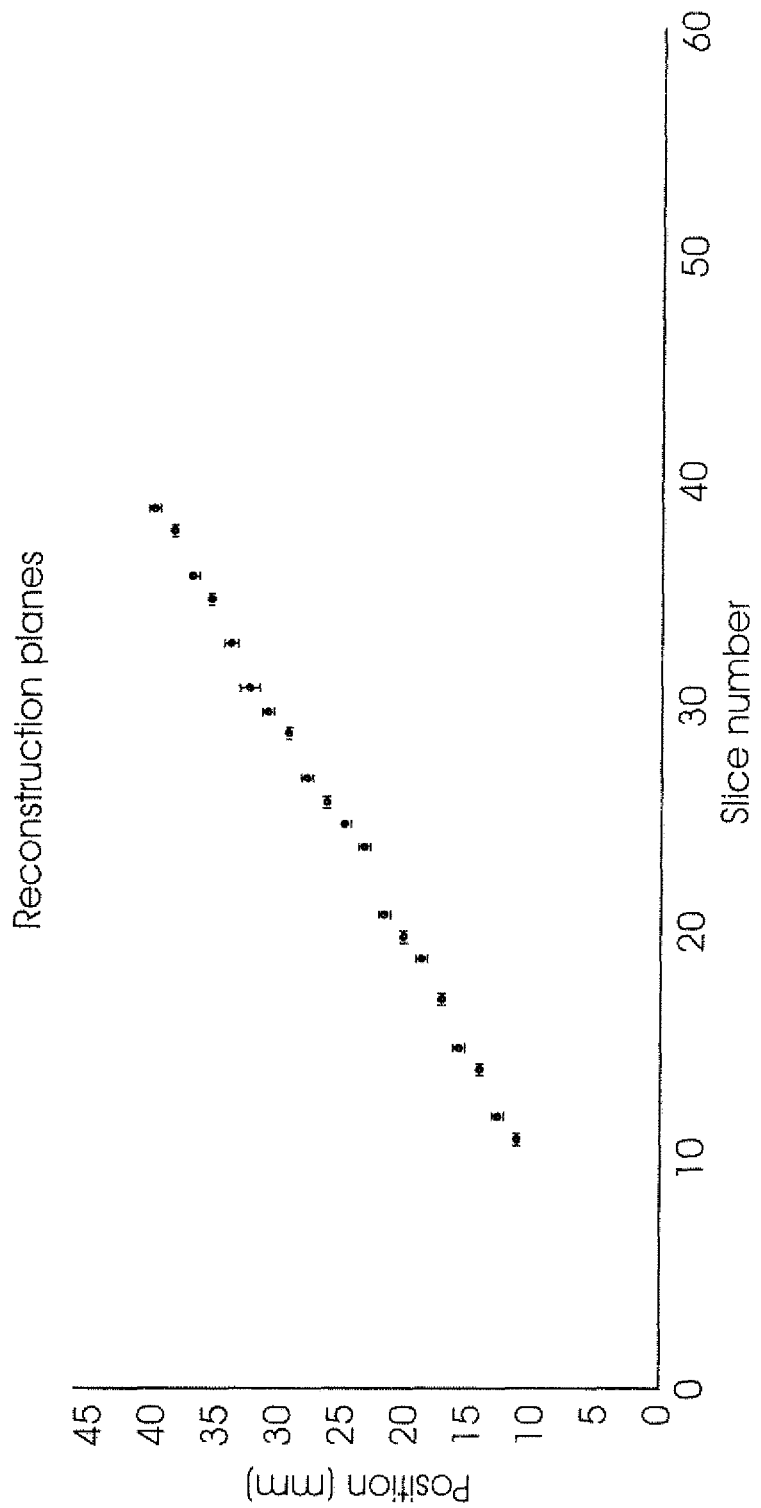
FIG. 3 is a graph of the obtained slice number against the best observed image of the calcifications in the slice.

The empty cells represent cases where the best seen images (most in focus images) were seen at other slice numbers. Therefore the empty cells are where the calcifications were not seen clearly or where not seen all. The results obtained in this table were then plotted, and is shown in FIG. 3. The plot shows he obtained slice number and the best seen image of the calcifications in the slice. The vertical error bars indicate the standard deviation between the slice number obtained and the actual position.

From both Table 1 and FIG. 3 it can be seen that there is a small error between the two parameters. The phantom design used was therefore found to be appropriate for determining the IRP. The error obtained would appear to be insignificant and the highest standard deviation obtained from the slice number and position in the slice is 0.8%. As a result it was found that the tomosynthesis reconstruction slice depths are as stated, within an uncertainty of +/−0.05 mm. In some of these images artefacts were present. The phantom design used was of assistance in determining the image reconstruction planes, and the errors were found to be small. The errors were interpreted and visualized by calculating the standard deviation, and most of the results compared well to the standard deviation—hence the conclusion that the errors were small. The tomosynthesis reconstruction was found to be in 1 mm slices.

It is important to realize that for the best image, the image reconstruction plane needs to be known or determined. Tomosynthesis images are prone to be noisy and have a lot of artefacts present. Artefacts degrade the quality of the image, for this reason it is important to verify the stated IRP as to minimize the amount of artefacts that can be present so to ensure optimal quality assurance testing. The proposed phantom design was used to evaluate the position of the image reconstruction planes. With the phantom used it was found that the reconstruction planes correlated well with the 1 mm thickness specified by the manufacturers.

The two main artefacts that were seen while analyzing the images were the vertical processing bar and the smear or out of plane artefact. The vertical processing bar artefacts are mostly seen on the edges of the phantom but the smear or out of plane artefact was seen on most of the slices along with partial volume artefacts.

Artefacts could be reduced by ensuring that a non-linear path is followed by the x-ray tube, so as to blur the out of plane objects in more than one plane. The linear single plane imaging pattern is limiting, creating a linear smear artefact which can be misleading, and dosing volumes of the breast where image reconstruction is compromised as all projection images do not contain the entire volume of reconstruction. If the x-ray source were made to follow an elliptical orbit with axis of rotation positioned some distance (approximately 2 cm) above the detector plane then minimal unnecessary tissue exposure would occur and the best focal plane would be within the volume of breast which is most likely to have pathology. The long axis of the ellipse could still be of the order of 15° at 60 cm above the detector plane, but the short axis would be minimised to just allow a single pixel on the detector between each projection image in the short axis direction. This would also limit projection x-rays from exposing a significant volume of the chest wall. The approximately 15 positions (24° spacing on the ellipse of rotation) of the x-ray tube would be such that they did not coincide in either of the axes.

The inventor is of the view that the phantom described above can in future be used routinely to verify the vertical positioning of reconstruction planes in DBT. The phantom that was developed could be used as an integral part of the quality program for DBT systems in order accurately to determine the actual image reconstruction planes (IRP) obtained during tomographic reconstruction.

It will be appreciated that the above is only one embodiment of the invention, and that there may be many variations without departing from the spirit and/or scope of the invention.

The invention claimed is:

1. A mammographic tomography test phantom for use in the verification of image reconstruction positions in digital breast tomosynthesis, the phantom including:
    a body made from an approximately tissue equivalent x-ray attenuating material;
    an upper spacer located on top of the body, and a lower spacer located below the body, the spacers being made from a substantially non-compressible material;
    and a plurality of x-ray opaque nodules located at predetermined positions, and at different depths, within the body,
    wherein the body comprises a plurality of layers located on top of one another, each layer including a particular number and/or configuration of x-ray opaque nodules that identify the particular layer, and which is different from the nodules located in the other layers.

2. The test phantom of claim 1 in which the positions of the nodules are dependent on their depth within the body.

3. The test phantom of claim 1 in which the body is made from wax.

4. The test phantom of claim 3 in which the plurality of layers located on top of one another are made of wax.

5. The test phantom of claim 3 in which the x-ray opaque nodules are impregnated into the wax body at predetermined intervals and locations.

6. The test phantom of claim 5 in which the x-ray opaque nodules are diagonally offset in order to reduce superposition of projection artefacts.

7. The test phantom of claim 1 in which the x-ray opaque nodules are diagonally offset in order to reduce superposition of projection artefacts.

8. The test phantom of claim 1 in which the x-ray opaque nodules is in the form of marble granules having diameters of between 100 and 300 μm.

9. The test phantom of claim 1 in which the x-ray opaque nodules is in the form of marble granules having diameters of between 200 and 250 μm.

10. The test phantom of claim 1 in which the spacers, which allow for accurate offset correction, are made from planar, substantially non-compressible material.

11. The test phantom of claim 10 in which the material from which each of the spacers is made is selected from the group including paper, card, Perspex® or another suitable plastic.

12. A method of verifying image reconstruction positions in digital breast tomosynthesis using a customized mammographic tomography test phantom, the method including the steps of:
    providing a test phantom including a body and a plurality of x-ray opaque granules located at predetermined positions within the body of the test phantom, wherein the body comprises a plurality of layers located on top of one another, each layer including a particular number and/or configuration of x-ray opaque nodules that identify the particular layer, and which is different from the nodules located in the other layers;
    locating the test phantom on a breast support of a mammography unit;
    procuring at least one image from the mammography unit; and
    analyzing the images in order to determine the image reconstruction planes.

13. The method of claim 12 in which the step of analyzing the images comprises the steps of:
    identifying a basal plane of the phantom;
    finding left and right edges and front and back edges of the phantom using edge detection;
    calculating magnification of the phantom in in-plane and front-back (Anterior-posterior) axes of an image set including the at least one image and determining a size of pixels of the image in the basal plane;
    stepping to a corner of an appropriate block where small opaque grains are positioned for each nominal slice of interest and a slice above and below each of these slices using the size of the pixels as determined above;
    stepping through a 6×6 mm sub-image using a single pixel step size in both directions sequentially and performing template matching using a symmetric, two dimensional, pixelated, Gaussian template of size 400× 400 μm;
    determining a maxima and full width half maxima of identified granules in the in-plane and front-back axes for all slices;
    confirming an identity of a slice position from the number and position of the maxima within the sub-images;
    determining contrast, relative resolution, and artefact distortion of the images due to in-plane blurring using ratios; and
    identifying from the ratios if the relative resolution is best within the slice of interest.

* * * * *